(12) United States Patent
Nakamura et al.

(10) Patent No.: US 11,357,403 B2
(45) Date of Patent: Jun. 14, 2022

(54) OPTICAL COHERENCE TOMOGRAPHY APPARATUS AND MEASUREMENT METHOD

(71) Applicant: FUJIFILM Corporation, Tokyo (JP)

(72) Inventors: Sohichiro Nakamura, Kanagawa (JP); Heijiro Hirayama, Kanagawa (JP); Takafumi Noguchi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 603 days.

(21) Appl. No.: 16/394,260

(22) Filed: Apr. 25, 2019

(65) Prior Publication Data

US 2019/0246906 A1 Aug. 15, 2019

Related U.S. Application Data

(63) Continuation of application No. PCT/JP2017/037415, filed on Oct. 16, 2017.

(30) Foreign Application Priority Data

Oct. 28, 2016 (JP) .............................. JP2016-211493

(51) Int. Cl.
*A61B 5/00* (2006.01)
*G01B 9/02091* (2022.01)
(Continued)

(52) U.S. Cl.
CPC .............. *A61B 5/0066* (2013.01); *A61B 5/00* (2013.01); *A61B 5/0073* (2013.01); *A61B 5/443* (2013.01);
(Continued)

(58) Field of Classification Search
CPC ....... A61B 5/00; A61B 5/0066; A61B 5/0073; A61B 5/443; G01B 2290/45; G01B 9/02091; G01N 21/17; G01N 21/4795
See application file for complete search history.

(56) References Cited

U.S. PATENT DOCUMENTS

2003/0103212 A1  6/2003  Westphal et al.
2005/0185192 A1  8/2005  Kim et al.
(Continued)

FOREIGN PATENT DOCUMENTS

CN  103961058 A  8/2014
CN  105942968 A  9/2016
(Continued)

OTHER PUBLICATIONS

Robles et al., "Molecular imaging true-colour spectroscopic optical coherence tomography", Nature Photonics, vol. 5, No. 12 Dec. 1, 2011, pp. 1-10.
(Continued)

*Primary Examiner* — Mark D Remaly
(74) *Attorney, Agent, or Firm* — Sughrue Mion, PLLC

(57) ABSTRACT

In an optical coherence tomography apparatus that generates a full-color optical coherence tomographic image, an image generation unit includes a correction processing unit that calculates an attenuation related value related to attenuation of signal intensity of the interference light of three R, G, and B colors in a first depth region and corrects the signal intensity of a second depth region deeper than the first depth region according to the attenuation related value to calculate a correction signal for the interference light and generates a full-color optical coherence tomographic image using the correction signals calculated for each of R, G, and B.

5 Claims, 15 Drawing Sheets

(51) Int. Cl.
*G01N 21/47* (2006.01)
*G01N 21/17* (2006.01)

(52) U.S. Cl.
CPC ......... *G01B 9/02091* (2013.01); *G01N 21/17* (2013.01); *G01N 21/4795* (2013.01); *G01B 2290/45* (2013.01)

(56) References Cited

U.S. PATENT DOCUMENTS

| | | |
|---|---|---|
| 2006/0063988 A1 | 3/2006 | Schurman et al. |
| 2006/0276696 A1 | 12/2006 | Schurman et al. |
| 2007/0014464 A1 | 1/2007 | Ohashi |
| 2009/0079993 A1 | 3/2009 | Yatagai et al. |
| 2009/0306520 A1 | 12/2009 | Schmitt et al. |
| 2011/0292400 A1 | 12/2011 | Fleming et al. |
| 2014/0125988 A1 | 5/2014 | Wang et al. |
| 2014/0211155 A1 | 7/2014 | Sakagawa et al. |
| 2014/0226150 A1 | 8/2014 | Colonna de Lega |
| 2015/0248770 A1 | 9/2015 | Hasegawa et al. |
| 2017/0224219 A1 | 8/2017 | Hirayama et al. |

FOREIGN PATENT DOCUMENTS

| | | |
|---|---|---|
| EP | 1892501 A2 | 2/2008 |
| JP | 2006-320380 A | 11/2006 |
| JP | 2007-523386 A | 8/2007 |
| JP | 2008-509728 A | 4/2008 |
| JP | 2008-194106 A | 8/2008 |
| JP | 2008-546430 A | 12/2008 |
| JP | 2010-127902 A | 6/2010 |
| JP | 2011-521747 A | 7/2011 |
| JP | 2013-108766 A | 6/2013 |
| JP | 2013-526395 A | 6/2013 |
| JP | 2014-095686 A | 5/2014 |
| JP | 2015-163862 A | 9/2015 |
| WO | 2007060973 A1 | 5/2007 |
| WO | 2012/004388 A1 | 1/2012 |
| WO | 2014085911 A1 | 6/2014 |
| WO | 2015045191 A1 | 4/2015 |
| WO | 2016067570 A1 | 5/2016 |

OTHER PUBLICATIONS

International Search Report dated Jan. 9, 2018 from the International Searching Authority in counterpart International Application No. PCT/JP2017/037415.
Written Opinion dated Jan. 9, 2018 from the International Bureau in counterpart International Application No. PCT/JP2017/037415.
International Preliminary Report on Patentability dated Feb. 28, 2019 from the International Bureau in counterpart International Application No. PCT/JP2017/037415.
Communication dated Jan. 25, 2021 from the European Patent Office in EP Application No. 17863455.6.
Communication dated Sep. 17, 2020 by the Korean Patent Office in application No. 10-2019-7012116.
Communication dated Mar. 10, 2020 from Japanese Patent Office in JP Application No. 2018-547574.
Communication dated Mar. 13, 2020 from European Patent Office in EP Application No. 17 863 455.6.
Communication dated Jul. 25, 2019 from the European Patent Office in application No. 17863455.6.
Hojjatoleslami, A., et al., "OCT skin image enhancement through attenuation compensation", Applied Optics, vol. 51, No. 21, 2012, pp. 4927-4935 (9 pages). Jul. 20, 2012.
Zhang, M., et al., "Dual-band Fourier domain optical coherence tomography with depth-related compensations", Biomedical Optics Express, vol. 5, No. 1, Dec. 10, 2013, 16 pages.
Vasefi, F., et al., "Toward in vivo diagnosis of skin cancer using multimode imaging dermoscopy: (II) Molecular mapping of highly pigmented lesions", Progress in Biomedical Optics and Imaging, SPIE, vol. 8947, Mar. 4, 2014, p. 89470J-1 to p. 89470J-11 (11 pages).
Liu, C.-S., et al., "True color blood flow imaging using a high-speed laser photography system", Optical Engineering, vol. 51, No. 10, Oct. 1, 2012, p. 103201-1 to p. 103201-9 (10 pages).
Briones-R., M., et al., "3D homogeneity study in PMMA layers using a Fourier domain OCT system", Optics and Lasers in Engineering, vol. 86, Jun. 14, 2016, pp. 181-196 (16 pages).
Communication dated Feb. 3, 2021 from The State Intellectual Property Office of P.R. of China in Machine Application No. 201780066353.3.
Communication dated Jul. 6, 2020 from European Patent Office in EP Application No. 17863455.6.

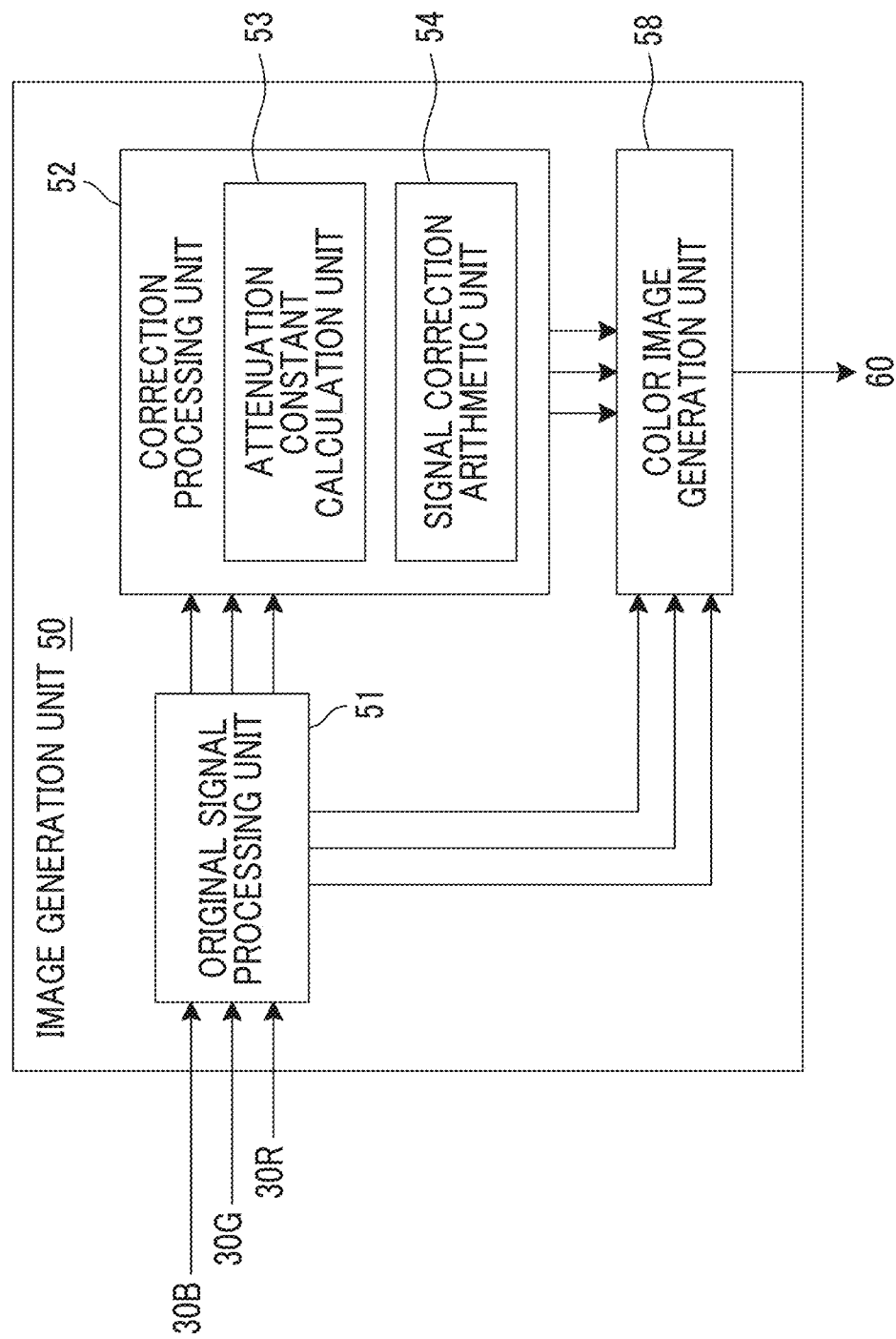

MODEL OF WHITE SKIN (PIGMENT 0wt%)

MODEL OF SKIN WITH STRONG YELLOW (PIGMENT 1wt%)

OPTICAL COHERENCE TOMOGRAPHY APPARATUS AND MEASUREMENT METHOD

CROSS-REFERENCE TO RELATED APPLICATIONS

This application is a continuation application of International Application No. PCT/JP2017/037415, filed Oct. 16, 2017, the disclosure of which is incorporated herein by reference in its entirety. Further, this application claims priority from Japanese Patent Application No. 2016-211493, filed Oct. 28, 2016, the disclosure of which is incorporated herein by reference in its entirety.

BACKGROUND OF THE INVENTION

1. Field of the Invention

The present invention relates to an optical coherence tomography apparatus, and more particularly, to an optical coherence tomography apparatus that can acquire a full-color optical coherence tomographic image. In addition, the invention relates to a measurement method using the optical coherence tomography apparatus.

2. Description of the Related Art

In the development of cosmetics or medicines and medical care, it is important to observe the internal state of the skin. In Europe, sales of cosmetics developed by animal experiments were banned entirely in the spring of 2013. Therefore, the necessity of a method for observing the human skin non-destructively and non-invasively is increasing.

An optical coherence tomography apparatus (hereinafter, referred to as an OCT apparatus in some cases) has been known as one of the non-destructive and non-invasive tomography methods. This is a tomography method using optical coherence, has been developed since the 1990's, is mainly applied to, for example, fundus examination, and uses near infrared light (1.3 μm or 1.5 μm).

A near infrared OCT apparatus which has been put into practical use has a depth resolution of about 20 μm. Therefore, the near infrared OCT apparatus is not suitable to observe the skin with high resolution. The layer structure of the skin includes keratin (a thickness of 10 to 30 μm), the epidermis (a thickness of 100 to 300 μm), and the dermis (a thickness of 1 mm or more) from the surface side and a resolution of 20 μm is not sufficient.

In contrast, a visible-light OCT apparatus that uses light from an ultraviolet range to a visible light range to improve resolution has been developed. An apparatus that can observe the aspect of the scattering of visible light in the skin is disclosed in, for example, JP2013-108766A, JP2015-163862A, and JP2007-523386A.

JP2013-108766A discloses a method in which super luminescent diode (SLD) light sources of each color generate low-coherent light of red (R), green (G), and blue (B) in the visible light range, foundation is applied to a skin replica, and the thickness of an uneven portion of the surface of the skin or a foundation layer is evaluated. However, since the RGB-OCT apparatus disclosed in JP2013-108766A is configured so as to comprise R, G, and B SLD light sources as the light sources in the visible light range, there are limitations in measurement at the wavelengths of the light sources provided in the apparatus and it is difficult to perform measurement in any color.

In contrast, since the OCT apparatus disclosed in JP2015-163862A has a light source unit including a white light source and a spectral shaping unit that cuts out any wavelength range, it is possible to acquire an optical coherence tomographic image using any wavelength in the visible light range.

In the field related to the human skin, a phenomenon called "yellowing" (Y. Ogura et al., J. Derm. Sci. 64 (2011) 45-52) in which the inside of the human skin turns yellow with advancing age has been known. It is considered that the phenomenon occurs due to, for example, the oxidation reaction of proteins in the dermis by the irradiation of the skin with ultraviolet rays. There is a demand for a measurement apparatus that can observe a color inside the skin.

There is a need to know a color inside an object not only in the field of the skin but also in various fields, such as systems including a vehicle body to which multiple layers of color materials are applied, art objects including paintings, food spoilage tests, medical diagnosis for the internal organs. Therefore, a strong demand for an apparatus that can acquire a full-color optical coherence tomographic image (hereinafter, referred to as an OCT image in some cases) of the inside of a measurement target and can be applied as a method for non-destructively quantifying a color inside a structure in a depth direction is expected.

However, for example, in JP2013-108766A and JP2015-163862A, the main intention is, for example, to compare simple OCT images to analyze the internal structure and the acquisition of a full-color image is not assumed.

In Francisco E. Robles, Christy Wilson, Gerald Grant & Adam Wax, "Molecular imaging true-color spectroscopic optical coherence tomography", Nature Photonics 5, 744-747 (1 Dec. 2011), an OCT image is obtained by reproducing the color of the skin of a living mouse. Specifically, an OCT image is measured in a state in which the skin of the back of an albino mouse with an extremely thin pigment is thinly stretched and is interposed between chambers to be fixed and it is possible to acquire information at a relatively large depth greater than 130 μm.

In addition, JP2007-523386A discloses an apparatus that can acquire a full-color OCT image.

SUMMARY OF THE INVENTION

Measurement light emitted to the surface of a measurement target enters the measurement target, is scattered inside the measurement target, returns to the surface side, and is detected by a detector through an optical component such as a lens. In this case, in practice, the absorption of light by a pigment in the measurement target or the attenuation of light by scattering occurs. Therefore, even in a case in which a signal (interference light) based on scattered light from the inside of the measurement target can be detected, the color of the scattered light is a pseudo color including the influence of light absorption and is not a true color.

In Francisco E. Robles, Christy Wilson, Gerald Grant & Adam Wax, "Molecular imaging true-color spectroscopic optical coherence tomography", Nature Photonics 5, 744-747 (1 Dec. 2011), the albino mouse with the skin which has a very thin pigment and is likely to transmit light is the measurement target and measurement is performed in a state in which the skin of the back of the mouse is stretched and fixed. Therefore, it is possible to capture an image with good quality. However, it is difficult to measure a deep region of, for example, the human skin or a coating film with a thick pigment, using the disclosed technique. In addition, it is considered that it is difficult to detect a true color. Further, in JP2007-523386A, the influence of, for example, the absorption of light by pigments in the measurement target is not considered. Therefore, even in a case in which a full-color OCT image can be acquired, the color of the full-color OCT image is just a pseudo color and it is difficult to observe a true color.

The invention has been made in view of the above-mentioned problems and an object of the invention is to provide an optical coherence tomography apparatus that can acquire a true color of the inside of a measurement target and a measurement method using the optical coherence tomography apparatus.

According to the invention, there is provided an optical coherence tomography apparatus comprising: a light source unit that emits low-coherent light with a red wavelength, low-coherent light with a green wavelength, and low-coherent light with a blue wavelength at the same time; a light splitting unit that splits the low-coherent light emitted from the light source unit into measurement light and reference light; a measurement light emission optical system that irradiates a measurement target with the measurement light; a multiplexing unit that multiplexes the reference light and light reflected from the measurement target in a case in which the measurement target is irradiated with the measurement light; an interference light detection unit that detects interference light of the reflected light and the reference light multiplexed by the multiplexing unit; and an image generation unit that generates an optical coherence tomographic image of the measurement target from the interference light detected by the interference light detection unit. The image generation unit calculates an attenuation related value related to attenuation of signal intensity of the interference light of the red wavelength, the green wavelength, and the blue wavelength in a first depth region, corrects the signal intensity of a second depth region deeper than the first depth region according to the attenuation related value to calculate a correction signal for the interference light, and generates a full-color optical coherence tomographic image using the correction signals calculated for each of the red wavelength, the green wavelength, and the blue wavelength.

In the optical coherence tomography apparatus according to the invention, the image generation unit may comprise: an attenuation constant calculation unit that calculates, as the attenuation related value, an attenuation constant for the signal intensity of the interference light of the red wavelength, the green wavelength, and the blue wavelength in the first depth region; and a signal correction arithmetic unit that corrects the signal intensity in the second depth region with the attenuation constant obtained by the attenuation constant calculation unit to calculate the correction signal.

The optical coherence tomography apparatus according to the invention may further comprise a spectral reflectance measurement unit that measures spectral reflectance of a surface of the measurement target. The image generation unit may comprise: a pigment concentration calculation unit that calculates a concentration of a pigment included in the first depth region from the spectral reflectance; and a signal correction arithmetic unit that calculates an amount of attenuation of light by the pigment as the attenuation related value on the basis of the concentration of the pigment obtained by the pigment concentration calculation unit and corrects the signal intensity in the second depth region to calculate the correction signal.

Here, the pigment concentration calculation unit may calculate a concentration of melanin as the pigment.

In the optical coherence tomography apparatus according to the invention, preferably, the red wavelength is 612 nm, the green wavelength is 537 nm, and the blue wavelength is 448 nm. Here, the wavelength is a peak wavelength of each color of the low-coherent light emitted from the light source unit.

In addition, the low-coherent light of each color emitted from the light source unit has a spectrum with a substantial Gaussian distribution shape having the peak wavelength as the center.

In the optical coherence tomography apparatus according to the invention, preferably, the interference light detection unit comprises an optical detector that detects interference light with the red wavelength, an optical detector that detects interference light with the green wavelength, and an optical detector that detects interference light with the blue wavelength, the optical detectors being separately provided.

The optical coherence tomography apparatus according to the invention may be a spectral-domain type or a time-domain type and is preferably the spectral-domain type in order to reduce the measurement time.

In particular, preferably, the optical coherence tomography apparatus according to the invention is the spectral-domain type having the following configuration. A first cylindrical lens that irradiates the measurement target with the measurement light in a linear shape is provided as the measurement light emission optical system. The optical coherence tomography apparatus further comprises a second cylindrical lens that is provided between the multiplexing unit and the interference light detection unit such that axes of cylinders of the first and second cylindrical lenses are orthogonal to each other. The interference light detection unit spectroscopically detects the interference light and the image generation unit converts a signal based on the interference light spectroscopically detected by the interference light detection unit into depth information using Fourier transform.

According to the invention, there is provided a measurement method using the optical coherence tomography apparatus according to the invention. The measurement method comprises: irradiating a measurement target with the measurement light; detecting the interference light of reference light and light reflected from the measurement target; generating an optical coherence tomographic image of the measurement target; displaying the optical coherence tomographic image on an image display device; calculating optical features on a surface of the measurement target or inside the measurement target from the interference light; and displaying the optical features on the image display device.

The optical features include, for example, intensity of reflected light at any position on the surface of the measurement target or inside the measurement target, a profile of the intensity of the reflected light in a depth direction, or an attenuation constant. Here, the intensity of the reflected light includes light caused by scattered light.

Examples of the measurement target include coating films, the human skin, plants, printed matters, paints which are not capable of being destroyed, and precious antique art objects.

Preferably, in a case in which the measurement target is the human skin, the optical coherence tomographic images of the human skin are generated before and after any cosmetic or medicine is applied to the human skin. Preferably, the optical features are calculated and the optical features and the optical coherence tomographic images before and after the application are displayed on the image display device. In addition, since it is difficult to fix the human skin so as not to move in micron order within the measurement time, it is preferable to perform measurement with one shot.

According to the optical coherence tomography apparatus of the invention, the image generation unit calculates the attenuation related value related to the attenuation of the signal intensity of the interference light of the red wavelength, the green wavelength, and the blue wavelength in the first depth region, corrects the signal intensity in the second depth region deeper than the first depth region according to the attenuation related value to calculate the correction signal for the interference light, and generates the full-color optical coherence tomographic image using the correction signals calculated for each of the red wavelength, the green wavelength, and the blue wavelength. Therefore, it is possible to acquire a true color of the inside of the measurement target.

BRIEF DESCRIPTION OF THE DRAWINGS

FIG. 4 is a block diagram illustrating specific Configuration Example 1 of an image generation unit.

DESCRIPTION OF THE PREFERRED EMBODIMENTS

Hereinafter, an embodiment of an optical coherence tomography apparatus (hereinafter, referred to as an OCT apparatus) according to the invention will be described with reference to the drawings.

Figure 1:
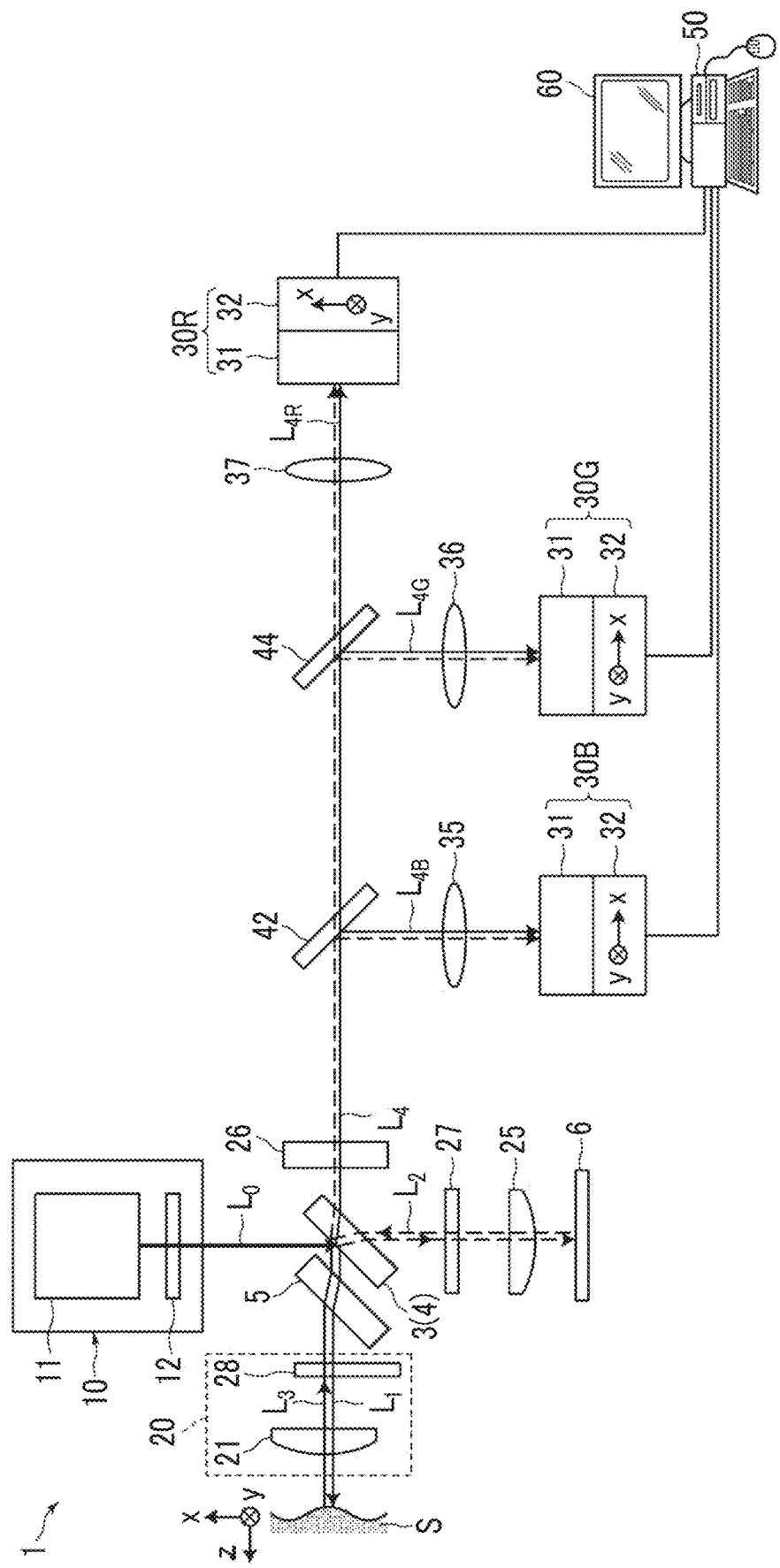
FIG. 1 is a diagram schematically illustrating the overall configuration of an optical coherence tomography apparatus according to an embodiment of the invention.

FIG. 1 is a diagram schematically illustrating the overall configuration of an OCT apparatus 1 according to an embodiment of the invention.

As illustrated in FIG. 1, the OCT apparatus 1 according to this embodiment includes a light source unit 10 that emits low-coherent light $L_0$, a light splitting unit 3 that splits the low-coherent light $L_0$ emitted from the light source unit 10 into measurement light $L_1$ and reference light $L_2$, a measurement light emission optical system 20 that irradiates a measurement target S (here, the human skin) with the measurement light $L_1$ in a linear shape, a multiplexing unit 4 that multiplexes the reference light $L_2$ and reflected light $L_3$ from the measurement target S in a case in which the measurement target S is irradiated with the measurement light $L_1$, dichroic filters 42 and 44 that separate interference light $L_4$ of the reflected light $L_3$ and the reference light $L_2$ multiplexed by the multiplexing unit 4 into R light, G light, and B light, a B interference light detection unit 30B that spectroscopically detects B light (B interference light) $L_{4B}$ in the interference light $L_4$, a G interference light detection unit 30G that spectroscopically detects G light (G interference light) $L_{4G}$, an R interference light detection unit 30R that spectroscopically detects R light (R interference light) $L_{4R}$, an image generation unit 50 that generates an optical coherence tomographic image (hereinafter, referred to as an OCT image) of the measurement target from the interference light detected by each of the interference light detection units 30R, 30G, and 30B, and an image display device 60 that displays the OCT image.

The light source unit 10 emits low-coherent light with a red wavelength, low-coherent light with a green wavelength, and low-coherent light with a blue wavelength at the same time and includes a single light source 11 that emits light including a wavelength range of, for example, at least 400 nm to 800 nm and a spectral shaping unit 12 that performs spectral shaping by cutting out a red wavelength range, a green wavelength range, and a blue wavelength range from the light emitted from the light source 11. The light source unit 10 emits the low-coherent light $L_0$ including low-coherent light with a red wavelength subjected to the spectral shaping, low-coherent light with a green wavelength subjected to the spectral shaping, and low-coherent light with a blue wavelength subjected to the spectral shaping.

The light source 11 is a white light source including a visible light range of at least 400 nm to 800 nm. In particular, a white light source that emits supercontinuum light is preferable.

Figure 2:
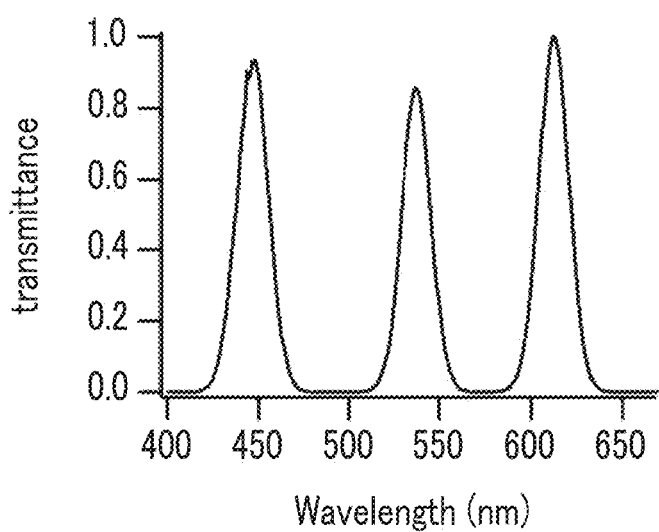
FIG. 2 is a diagram illustrating a transmittance profile of a spectral shaping unit included in a light source unit.

The spectral shaping unit 12 is a Gaussian filter that cuts out any wavelength range from light in a band including the entire visible light range emitted from the light source 11 and spectrally shapes the wavelength range into a Gaussian distribution. It is preferable to use a Gaussian filter that spectrally shapes each of at least three primary colors of red, green, and blue and transmits the spectrally shaped colors at the same time, and has, for example, a transmission spectrum illustrated in FIG. 2 having a plurality of peaks in order to obtain a full-color image. As illustrated in FIG. 2, in the filter having a transmission spectrum with a plurality of peaks, each peak has the Gaussian distribution.

Any combination of R, G, and B wavelength ranges may be used as long as it can reproduce a full color. In particular, it is preferable that the peak wavelength of blue is 448 nm, the peak wavelength of green is 537 nm, and the peak wavelength of red is 612 nm. WA Thornton (1973) used computer programs to generate a large number of metameric pairs and to calculate the frequency distribution of the crossing wavelengths of the same white and found that the crossing wavelengths were concentrated in the vicinity of 448 nm, 537 nm, and 612 nm. The reproduction performance of white is significantly improved by the use of these wavelengths.

In this configuration, the light source unit includes the white light source and the spectral shaping unit. However, instead of this configuration, the light source unit may comprise a light source that emits R light, a light source that emits G light, a light source that emits B light. R, G, and B SLDs are preferable as the light sources.

In this embodiment, the light splitting unit 3 that splits the low-coherent light $L_0$ emitted from the light source unit 10 into the measurement light $L_1$ and the reference light $L_2$ is a quartz plate (hereinafter, referred to as the quartz plate 3 in some cases) and also functions as the multiplexing unit 4 that multiplexes the reference light $L_2$ and the reflected light $L_3$ of the measurement light $L_1$ emitted to the measurement target S. The low-coherent light $L_0$ is incident on an incident surface of the quartz plate 3 (4) at a predetermined incident angle (for example, 45°) that is not 0°. The measurement target S is irradiated with light reflected from the incident surface in the low-coherent light $L_0$ incident on the incident surface of the quartz plate 3 (4) as the measurement light $L_1$. Light transmitted through the quartz plate 3 (4) in the low-coherent light $L_0$ incident on the incident surface is incident as the reference light $L_2$ on a reflecting member 6.

For example, a general beam splitter and a general half mirror can be used as the light splitting unit 3 and the multiplexing unit 4, respectively. However, since the quartz plate is inexpensive and has a very low reflectance of about 4%, the use of the reflected light as the measurement light makes it possible to suppress the stimulation of the human skin, which is very preferable.

In addition, a quartz plate 5 is provided on an optical path of the measurement light $L_1$ in order to improve the symmetry of an optical system such as an optical path length. The quartz plate 5 for dispersion compensation has the same shape as the quartz plate 3 which is the light splitting unit and is provided so as to be substantially parallel to the quartz plate 3.

The measurement light emission optical system 20 is provided between the quartz plate 3 (4) and the measurement target S. The measurement light emission optical system 20 includes a first cylindrical lens 21 and is configured such that the measurement light $L_1$ is emitted in a linear shape extending in the direction y of one axis (a depth direction of the plane of paper in FIG. 1) on the surface of the measurement target S by the first cylindrical lens 21. The first cylindrical lens 21 has, for example, a focal length f=75 mm. Since the measurement light $L_1$ is emitted in a linear shape, a two-dimensional tomographic image can be obtained by one exposure operation in a short time.

In addition, the measurement light emission optical system 20 may comprise other optical systems such as a polarizer and a zoom lens which are not illustrated in the drawings.

The reflecting member 6 is, for example, a mirror and is provided so as to reflect the reference light $L_2$ split by the light splitting unit 3 to the multiplexing unit 4.

The multiplexing unit 4 multiplexes the reference light $L_2$ reflected from the reflecting member 6 and the reflected light $L_3$ from the measurement target S and emits the light to the interference light detection unit. As described above, in this embodiment, the multiplexing unit 4 is a quartz plate that also functions as the light splitting unit 3.

The lengths of the optical paths through which the reference light $L_2$ and the reflected light $L_3$ are transmitted and wavelength dispersion characteristics need to be the same in order to improve the coherence between the reference light $L_2$ and the reflected light $L_3$. Therefore, in this embodiment, a cylindrical lens 25 having, for example, a focal length f=75 mm which is the same as the first cylindrical lens 21 provided on the optical path of the measurement light $L_1$ (and the reflected light $L_3$ of the measurement light $L_1$) is provided on the optical path of the reference light $L_2$. In addition, in the measurement light $L_1$ emitted to the measurement target S, the amount of reflected light $L_3$ which is reflected from the measurement target S and returns to the multiplexing unit 4 is very small. A dimming filter (ND filter) 27 for reducing the intensity of the reference light $L_2$ is provided on the optical path of the reference light $L_2$ in order to secure the symmetry between the reference light $L_2$ and the reflected light $L_3$. In addition, an optical path adjustment mechanism 28 is provided on the optical path of the measurement light $L_1$ in order to compensate for the difference between the optical paths caused by the dimming filter 27. The optical path adjustment mechanism 28 is not particularly limited as long as it can compensate for the difference between the optical paths caused by the dimming filter 27. Specifically, a quartz plate whose thickness has been adjusted can be used. As such, it preferable that an optical system is configured such that the length of the optical path of the reference light $L_2$ is equal to the length of the optical path of the measurement light $L_1$ emitted to a reference point (here, the surface of the measurement target S) of the measurement target S.

Three interference light detection units 30B, 30G, and 30R further disperse a B component, a G component, and an R component of the interference light $L_4$ of the reflected light $L_3$ and the reference light $L_2$ multiplexed by the multiplexing unit 4, respectively, and detect each wavelength component and include a spectroscope 31 that disperses the interference light $L_4$ and a two-dimensional optical detector 32.

Figure 3A:
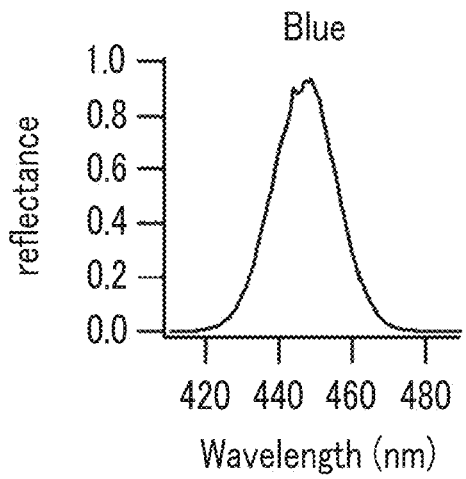
FIG. 3A is a diagram illustrating a reflectance profile of a first dichroic filter.
Figure 3B:
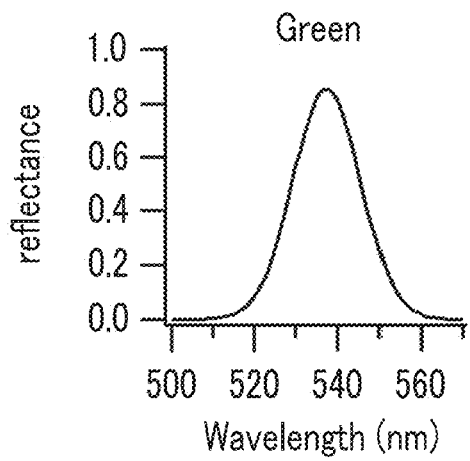
FIG. 3B is a diagram illustrating a reflectance profile of a second dichroic filter.
Figure 3C:
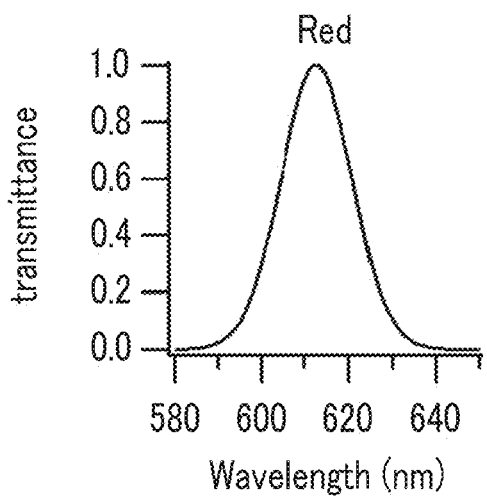
FIG. 3C is a diagram illustrating a transmittance profile of the second dichroic filter.

The first dichroic filter 42 reflects the B light and transmits other colors. The second dichroic filter 44 reflects the G light and transmits other colors. In a case in which the light source unit 10 comprises a Gaussian filter with the profile illustrated in FIG. 2, the dichroic filter 42 has a reflectance profile illustrated in FIG. 3A and reflects the B light. The dichroic filter 44 has a reflectance profile illustrated in FIG. 3B and reflects the G light. The dichroic filter 44 has a transmittance profile illustrated in FIG. 3C and transmits the R light.

The B interference light detection unit 30B is provided at a position that receives the B interference light $L_{4B}$ reflected from the first dichroic filter 42. The G interference light detection unit 30G is provided at a position that receives the G interference light $L_{4G}$ reflected from the second dichroic filter 44. The R interference light detection unit 30R is provided at a position that receives the R interference light $L_{4R}$ transmitted through the second dichroic filter 44.

Various known techniques can be used as the spectroscope 31. For example, the spectroscope 31 may be a diffraction grating. The optical detector 32 may be, for example, a two-dimensional optical sensor in which light receiving elements, such as CCDs or photodiodes, are two-dimensionally arranged.

Since each color is detected by the optical detectors 32 of the individual interference light detection units 30B, 30G, and 30R, it is possible to increase wavelength resolution. As a result, it is possible to acquire an OCT image at the depth greater than 130 μm from the surface.

In addition, even in a configuration in which interference light of three colors is detected by one interference light detection unit, in a case in which the number of pixels in the two-dimensional optical sensor is the same as that in three optical detectors, it is possible to acquire an OCT image in the same depth range.

Further, a second cylindrical lens (in this example, the focal length f is 150 mm) 26 and imaging lenses (the focal length f is 50 mm) 35, 36 and 37 are provided between the multiplexing unit 4 and the interference light detection units 30B, 30G, and 30R.

The second cylindrical lens 26 is provided such that an axis (cylindrical axis) of a cylinder in a length direction intersects that in the first cylindrical lens 21 which is provided in the measurement light emission optical system 20 and emits light in a linear shape.

The light receiving elements of the XY-axis two-dimensional optical sensor forming the optical detector 32 are arranged in the two-dimensional XY direction schematically illustrated in the optical detector 32 in FIG. 1 and the spectroscope 31 is provided such that it disperses the interference light $L_4$ and the light receiving elements arranged in the X-axis direction in the two-dimensional optical sensor detect the amount of light for each wavelength. In the two-dimensional optical sensor, interference light caused by the reflected light of linear measurement light at each position in a line direction (y direction) in a measurement surface is incident on the light receiving elements arranged in the Y-axis direction. Fourier transform can be performed for light in the x direction compressed by the first cylindrical lens 21 to obtain information in the depth direction (z direction). That is, in the OCT apparatus 1, light components having information in the plane direction (y direction) and information in the depth direction (z direction) of the measurement target are incident on the two-dimensional optical sensor at the same time. Therefore, a two-dimensional optical coherence tomographic image in the y direction and the z direction can be acquired by one exposure (one-shot) operation.

Figure 5:
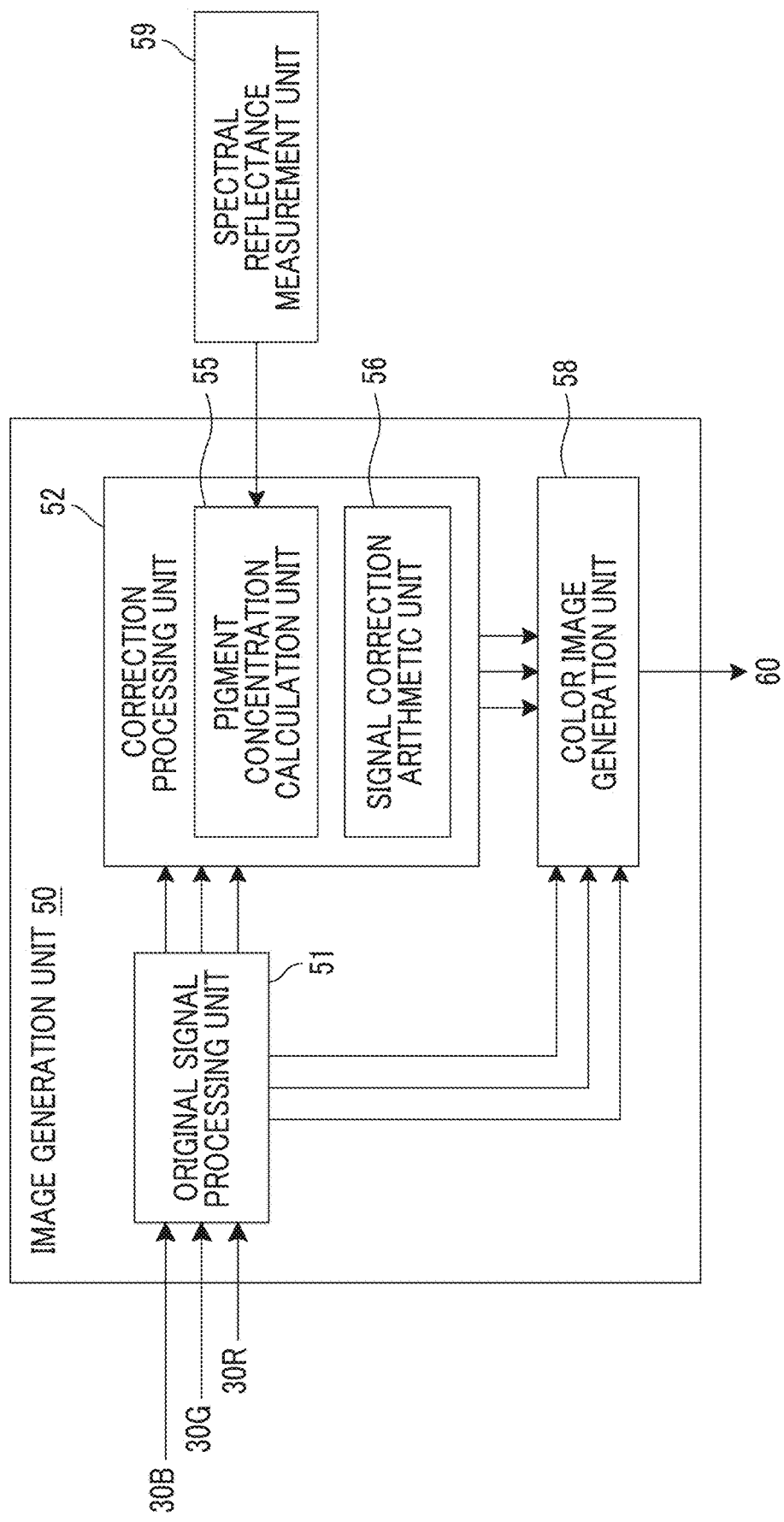
FIG. 5 is a block diagram illustrating specific Configuration Example 2 of the image generation unit.

The image generation unit 50 can be configured by, for example, a personal computer and a program that is incorporated into the computer in order to cause the computer to perform an image generation process. FIGS. 4 and 5 are block diagrams illustrating a first configuration example and a second configuration example of the image generation unit 50, respectively.

As illustrated in FIGS. 4 and 5, the image generation unit 50 comprises an original signal processing unit 51 that generates optical coherence tomographic image data (OCT image data) of each color from the interference light of each color detected by the interference light detection units 30B, 30G, and 30R, a correction processing unit 52 that calculates an attenuation related value related to the signal attenuation of signal intensity of interference light of a red wavelength, a green wavelength, and a blue wavelength in a first depth region from the OCT image data of each color and corrects the signal intensity of a second depth region deeper than the first depth region according to the attenuation related value to calculate a correction signal for interference light, and a color image generation unit 58 that generates a full-color optical coherence tomographic image using the correction signals calculated for each of the red wavelength, the green wavelength, and the blue wavelength.

Figure 8A:
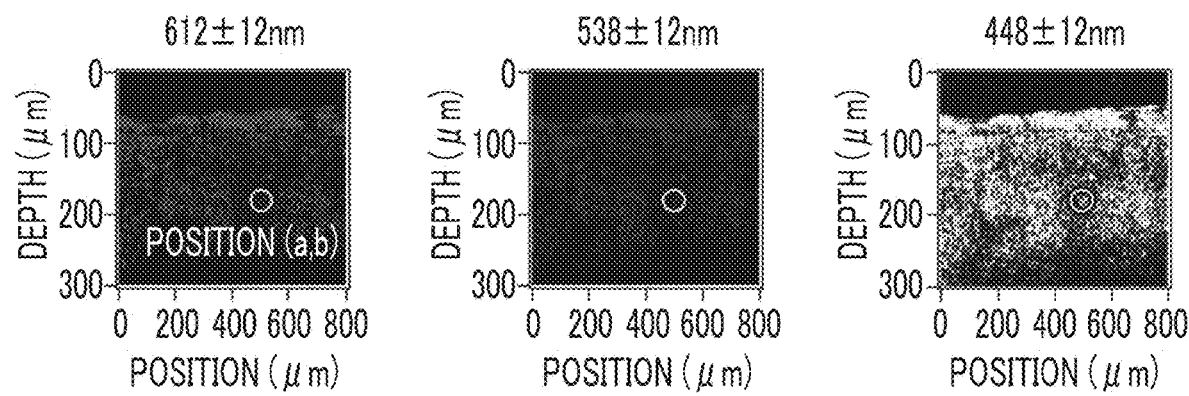
FIG. 8A is a diagram illustrating a colorizing procedure (Part 1).

The original signal processing unit 51 acquires reflection information at the depth position z of the measurement target S by performing frequency analysis for the interference light $L_4$ detected by the interference light detection units 30B, 30G, and 30R, specifically, by converting a wavelength in an intensity spectrum for each wavelength detected by the light receiving elements which are arranged in the X-axis direction in the two-dimensional optical sensor into a wave number and performing Fourier transform (FT), and generates OCT image data of each color (see FIG. 8A).

The correction processing unit 52 calculates the attenuation related value related to the signal attenuation of the first depth region in the depth direction of the measurement target from the OCT image data of each color. Here, the attenuation related value is related to the attenuation of the measurement light and the reflected light (scattered light) inside the measurement target and is not particularly limited as long as it is a factor that can be applied to correct the intensity of a detection signal from the second depth region. Specifically, for example, the attenuation related value is an attenuation function in the first depth region or pigment concentration in the first depth region.

Here, assuming that the measurement target includes the first depth region and the second depth region deeper than the first depth region in the depth direction from the surface of the measurement target, the signal of the second depth region is corrected using the attenuation related value acquired from the first depth region. However, assuming that the depth direction of the measurement target is subdivided into n layers from the surface to an n-th region, the signal of an i-th region may be corrected using an attenuation related value acquired from an (i-1)-th region. The signal of the i-th region is affected by the attenuation of light from the surface to the (i-1)-th region. Therefore, in the case of a signal correction operation, attenuation related values including the attenuation related values for correction from the surface to the (i-1)-th region may be calculated.

Specific examples of the first and second depth regions in the measurement target will be described with reference to FIGS. 6A, 6B, and 7.

Figure 6A:
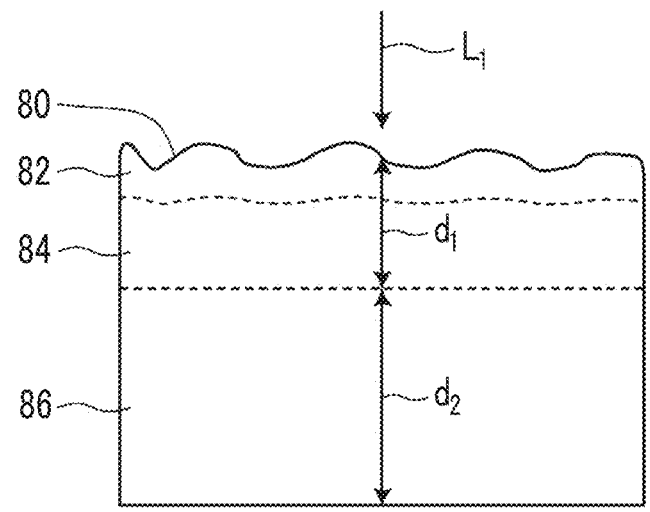
FIG. 6A is a cross-sectional view schematically illustrating a skin including first and second depth regions.
Figure 6B:
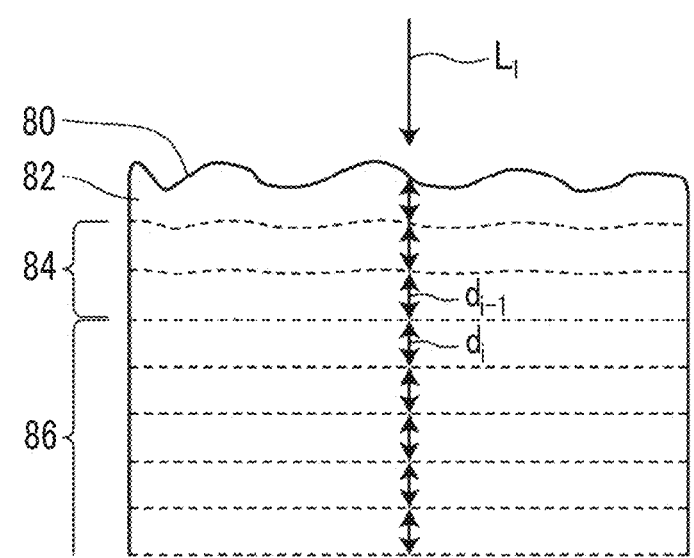
FIG. 6B is a cross-sectional view schematically illustrating a skin including first and n-th depth regions.

First, a case in which the measurement target is the skin will be described with reference to cross-sectional views of FIGS. 6A and 6B schematically illustrating the skin.

As illustrated in FIG. 6A, the skin has keratin 82, the epidermis 84, and the dermis 86 arranged from a skin surface 80 irradiated with the measurement light $L_1$. For example, it is assumed that a region from the skin surface 80 to the epidermis 84 is a first depth region $d_1$ and the dermis 86 is a second depth region $d_2$. Here, the keratin 82 is thinner than other layers and is transparent, and the attenuation of light in the keratin 82 is small. Therefore, the keratin 82 is integrally treated with the epidermis. A signal of the second depth region $d_2$ is corrected using an attenuation related value in the first depth region $d_1$. The ranges of the first depth region $d_1$ and the second depth region $d_2$ and/or the boundary between the regions may be appropriately determined from the OCT image or the one-dimensional profile of the measurement light in the depth direction. In addition, the regions may be determined from, for example, an average thickness from the skin surface to the dermis 86.

Further, as illustrated in FIG. 6B, the measurement target may be subdivided into a plurality of regions, for example, three or more regions in the depth direction from the skin surface 80. In this case, each depth region may be determined in the depth direction regardless of, for example, the boundary between the epidermis and the dermis. The signal of the second depth region $d_2$ is corrected using the attenuation related value obtained from the first depth region $d_1$. As described above, the signal of the i-th region may be corrected using the attenuation related value obtained from the (i-1)-th region. Each depth region may be determined at a regular interval in the depth direction. Each depth region may be determined such that, as the depth from the skin increases, the interval increases.

Figure 7:
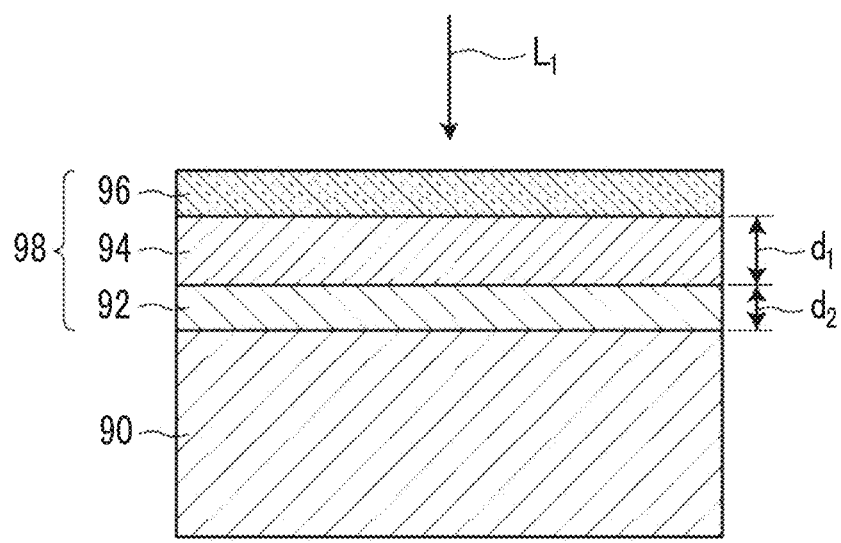
FIG. 7 is a cross-sectional view schematically illustrating a coating film with a three-layer structure.

A case in which the measurement target a coating film will be described with reference to a cross-sectional view of FIG. 7 schematically illustrating a coating film.

FIG. 7 illustrates a configuration in which a coating film 98 including an underlying layer 92, a coloring layer 94, and a clear coating layer 96 is provided on a surface of a base (for example, a body of a car) 90 from the base 90. The thickness of each layer is, for example, about 100 μm. In a case in which the clear coating layer 96 is transparent and there is little light attenuation, as illustrated in FIG. 7, the clear coating layer 96 from the surface side of the coating film 98 which is irradiated with the measurement light $L_1$ may be ignored, the coloring layer 94 may be the first depth region $d_1$, and the underlying layer 92 may be the second depth region $d_2$. In the case of the coating film including a plurality of layers illustrated in FIG. 7, the boundary between the layers can be recognized from an acquired OCT image. Each region may be designated by an observer and the boundary in the image may be calculated by image processing and may be automatically determined.

The measurement target is not limited to the object in which the boundary between layers can be clearly determined, such as the skin including the epidermis and the dermis illustrated in FIGS. 6A and 6B or the coating film including a plurality of layers illustrated in FIG. 7 and may be an object in which the boundary between layers is not observable in a measurement depth direction. In a case in which a depth region (second depth region) in which the observer is interested is influenced by, for example, light attenuation in a depth region (first depth region) shallower than the depth region (second depth region), the measurement target may be regarded as including the first depth region and the second depth region.

In a case in which an optical coherence tomographic image is acquired, the surface of the measurement target is irradiated with the measurement light. In a case in which the measurement light enters the measurement target, as the measurement light travels in the depth direction, that is, as the depth increases, the amount of light is attenuated by the absorption of light by pigments in the measurement target and scattering in the internal structure. That is, the amount of light reaching a deeper region becomes smaller. For return light from the deep region, the absorption of light by pigments and scattering in the internal structure occur again in an optical path to the surface of the measurement target.

As a result, the detected light intensity is further attenuated. For example, in a case in which only a specific color is absorbed by the absorption of light by a specific pigment, information on a specific color in the original data is likely to be lost. That is, in the full-color OCT image reproduced by the original data, the color of a deep portion of the measurement target is influenced by the attenuation of light in the upper layer (region). The image generation unit 50 of the OCT apparatus 1 comprises the correction processing unit 52 and the correction processing unit 52 is configured so as to calculate an attenuation related value and a correction signal and to generate a full-color image using the correction signal. Therefore, it is possible to reproduce a true color in the measurement target.

As described above, the original signal processing unit 51 of the image generation unit 50 performs Fourier transform for a wave number to obtain reflection information at the depth z. Reflection information at any depth position z includes the optical features of the measurement target. For example, the optical features include the intensity of reflected light on the surface of the measurement target, the intensity of reflected light including scattered light at any depth, a one-dimensional profile in the depth direction, and an attenuation constant which will be described below. It is desirable that the image generation unit 50 is configured so as to calculate any optical features in addition to the generation of the OCT image.

The image display device 60 displays the full-color OCT image generated by the image generation unit 50 or the optical features of the measurement target. The image display device 60 may be, for example, a liquid crystal display. The OCT image and optical features of the measurement target are displayed on the image display device 60 such that the observer can see the image of the measurement target or the digitized measurement target and evaluate the measurement target. The display of the OCT image and the display of the optical features on the image display device 60 may be performed at the same time or sequentially.

A specific example of the configuration of the correction processing unit 52 in the image generation unit 50 will be described. FIG. 4 illustrates a first configuration example. The correction processing unit 52 of the image generation unit 50 illustrated in FIG. 4 comprises an attenuation constant calculation unit 53 that calculates, as the attenuation related value, an attenuation constant for the signal intensity of the interference light of R, G, and B in the first depth region and a signal correction arithmetic unit 54 that corrects the signal intensity in the second depth region with the attenuation constant obtained by the attenuation constant calculation unit 53 to calculate the correction signal.

FIG. 5 illustrates a second configuration example of the correction processing unit 52. The image generation unit 50 illustrated in FIG. 5 comprises a pigment concentration calculation unit 55 that calculates the concentration of a pigment included in the first depth region from the spectral reflectance measured on the surface (the same position as that where the OCT image is acquired) of the measurement target S and a signal correction arithmetic unit 56 that calculates the amount of attenuation of light by the pigment as the attenuation related value on the basis of the concentration of the pigment obtained by the pigment concentration calculation unit 55 and corrects the signal intensity in the second depth region to calculate the correction signal. In the configuration comprising the correction processing unit 52 according to the second configuration example, the OCT apparatus further comprises a spectral reflectance measurement unit 59 that acquires spectral reflectance on the surface of the measurement target. In addition, the spectral reflectance measurement unit 59 may be separately provided. The spectroscope 31 in any one of the interference light detection unit 30B, 30G, or 30R in the OCT apparatus 1 illustrated in FIG. 1 may also function as the spectral reflectance measurement unit 59.

In any configuration, the attenuation related value can be calculated from the OCT image data (original data) of each color obtained by the original signal processing unit 51, a correction process can be performed for the original data of each color to create corrected image data, and the color image generation unit 58 can generate a full-color OCT image on the basis of the corrected image data of each color. Alternatively, the color image generation unit 58 may generate a full-color OCT image on the basis of the original data of each color obtained by the original signal processing unit 51 and a correction process may be performed for the full-color OCT image on the basis of signal correction data obtained by the correction processing unit 52. That is, the correction signal calculated by the signal correction arithmetic unit 54 or 56 may be the corrected image data of each color or the signal correction data applied to the full-color OCT image.

The procedure of generating a full-color image from the OCT image data of R, G, and B is as follows.

Here, a case in which a color image is generated using the optical coherence tomographic image data of each color illustrated in FIG. 8A obtained by the original signal processing unit 51 will be described. However, a full-color image may be generated using the corrected image data of each color by the same procedure as described above.

Figure 8B:
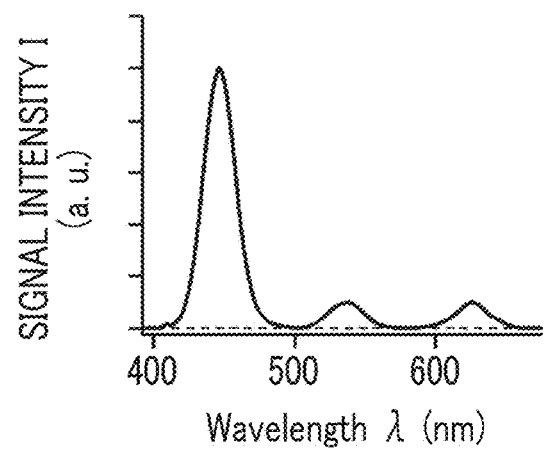
FIG. 8B is a diagram illustrating the colorizing procedure (Part 2).

A scattered light spectrum $I(\lambda)$ is calculated from a corresponding position of the OCT image data of each color. The scattered light spectrum $I(\lambda)$ is calculated at each corresponding position (a, b) in each image illustrated in FIG. 8A (FIG. 8B).

Figure 8C:
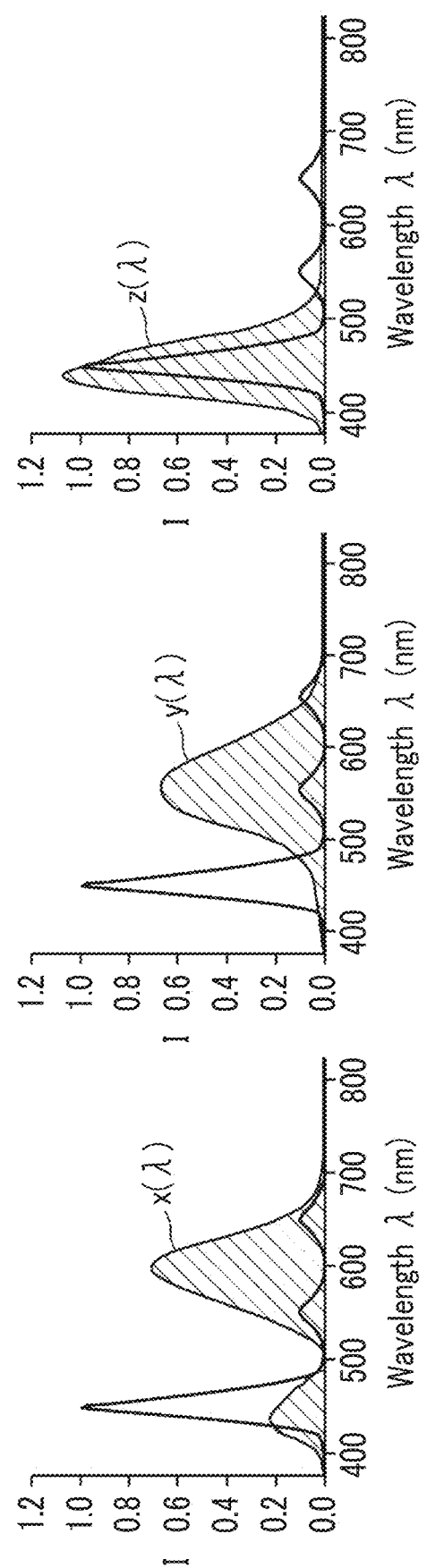
FIG. 8C is a diagram illustrating the colorizing procedure (Part 3).

Color-matching functions $x(\lambda)$, $y(\lambda)$, and $z(\lambda)$ are applied to the scattered light spectrum $I(\lambda)$ at each position to integrate the scattered light spectrum $I(\lambda)$ (FIG. 8C, the following Expression 1). In this way, stimulus values X, Y, and Z in the International Commission on Illumination (CIE)-XYZ color system are obtained.

$$X = f(I(\lambda) \times x(\lambda)) d\lambda$$

$$Y = f(I(\lambda) \times y(\lambda)) d\lambda$$

$$Z = f(I(\lambda) \times z(\lambda)) d\lambda \quad \text{[Expression 1]}$$

The stimulus values X, Y, and Z are converted into values in an RGB color system by an operation represented by the following Expression 2 and are then changed to 256 levels to gradation to calculate full-color tomographic image data.

$$\begin{pmatrix} R' \\ G' \\ B' \end{pmatrix} = \begin{pmatrix} 3.241 & -1.537 & -0.4986 \\ -0.9692 & 1.876 & 0.0416 \\ 0.0556 & -0.2040 & 1.051 \end{pmatrix} \begin{pmatrix} X \\ Y \\ Z \end{pmatrix} \quad \text{[Expression 2]}$$

$$R = \text{floor}\left[\left(\frac{R'}{Rw}\right)^{\frac{1}{\gamma}} \times 255\right]$$

$$G = \text{floor}\left[\left(\frac{G'}{Gw}\right)^{\frac{1}{\gamma}} \times 255\right]$$

$$B = \text{floor}\left[\left(\frac{B'}{Bw}\right)^{\frac{1}{\gamma}} \times 255\right]$$

$\gamma = 2.2$, $Rw$, $Gw$, $Bw = 80000$

In addition, in a case in which scattering intensity (interference light intensity) from the measurement target is low, data corresponding to several pixels may be merged to perform an averaging process. In Expression 2, the content of the 3×3 matrix is a conversion expression in the case of a D65 light source and is determined according to the optical system and color reproduction conditions. Therefore, the content of the 3×3 matrix is variable. Here, the values of Rw, Gw, and Bw are 80000. However, these values can be changed depending on a measurement system or a white standard sample.

The inventors found that a full-color OCT image of a commercially available color checker was acquired by the above-mentioned method and white and yellow of the color checker could be accurately reproduced.

Next, the result of capturing a full-color OCT image of a model skin will be described.

Figure 9:
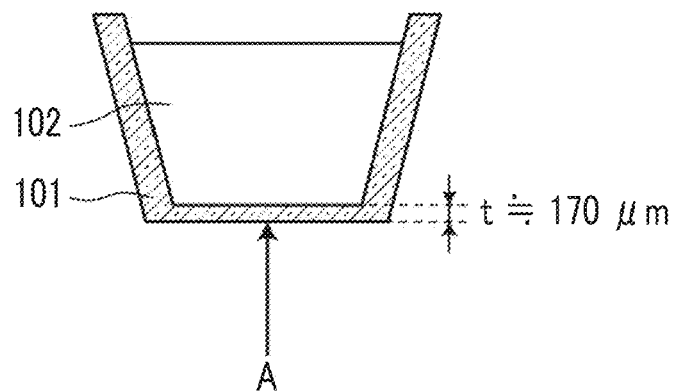
FIG. 9 is a diagram schematically illustrating a model skin.
Figure 10:
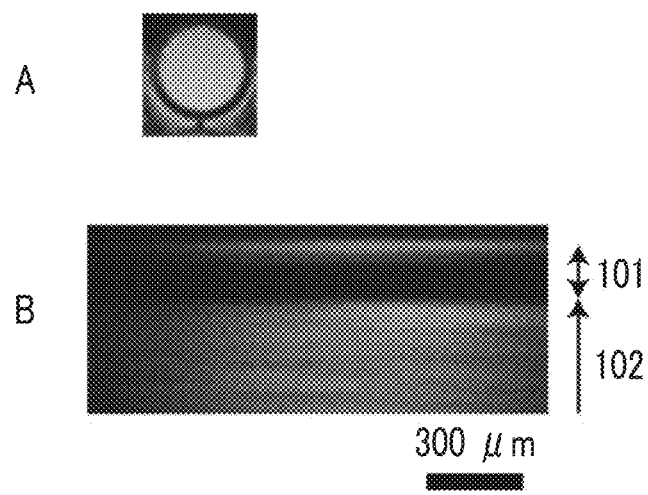
FIG. 10 is a diagram illustrating the outward appearance (A) of a white skin model and an OCT image (B).
Figure 11:
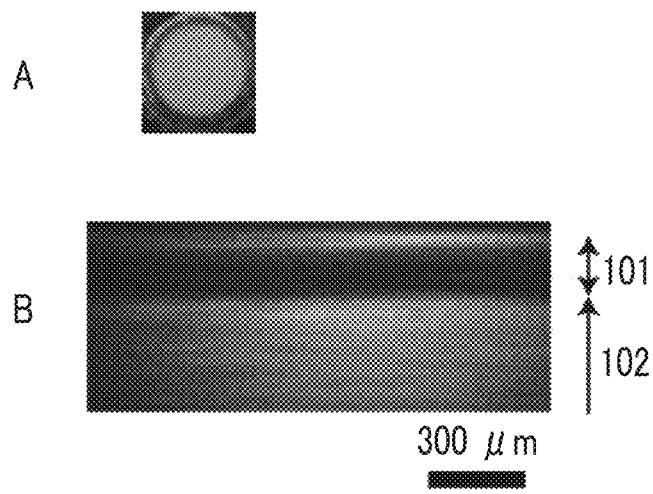
FIG. 11 is a diagram illustrating the outward appearance (A) of a skin model with strong yellow and an OCT image (B).

FIG. 9 is a diagram schematically illustrating the configuration of the model skin. The model skin was prepared by placing gelatin 102 containing polystyrene particles (a particle size of 200 nm and a concentration of 0.8 wt %) and 0 wt % or 0.3 wt % of yellow pigment in a glass container 101 having a bottom thickness t of about 170 μm. Since the skin has a multi-layer structure of the epidermis and the dermis, the glass container 101 was regarded as the epidermis and the gelatin 102 in the container 101 was regarded as the dermis. FIGS. 10 and 11 illustrate the outward appearance A of the bottom of the glass container 101 illustrated in FIG. 9 and a full-color OCT image B captured from a lower side A (in this case, no correction process is performed).

FIG. 10 illustrates a white skin model in which no yellow pigments are included in gelatin (0 wt % of pigment) and FIG. 11 illustrates a skin model with strong yellow containing 0.3 wt % of yellow pigment in gelatin. It was found that a signal (backscattered light) was observed from the surface of glass simulating the epidermis and a transparent region below the glass was dark in any of the OCT images illustrated in FIGS. 10 and 11. In addition, a signal from gelatin simulating the dermis was observed from a deep region.

Colors are not clear in FIGS. 10 and 11 illustrated in gray scale. However, it was found that, in color images corresponding to FIGS. 10 and 11, a gelatin region corresponding to the dermis could be displayed in white in a white skin model, a gelatin region corresponding to the dermis could be displayed in yellow in a skin with model with strong yellow, and the difference in color at a deep position corresponding to the dermis in the model skin could be represented by a color image.

Figure 12:
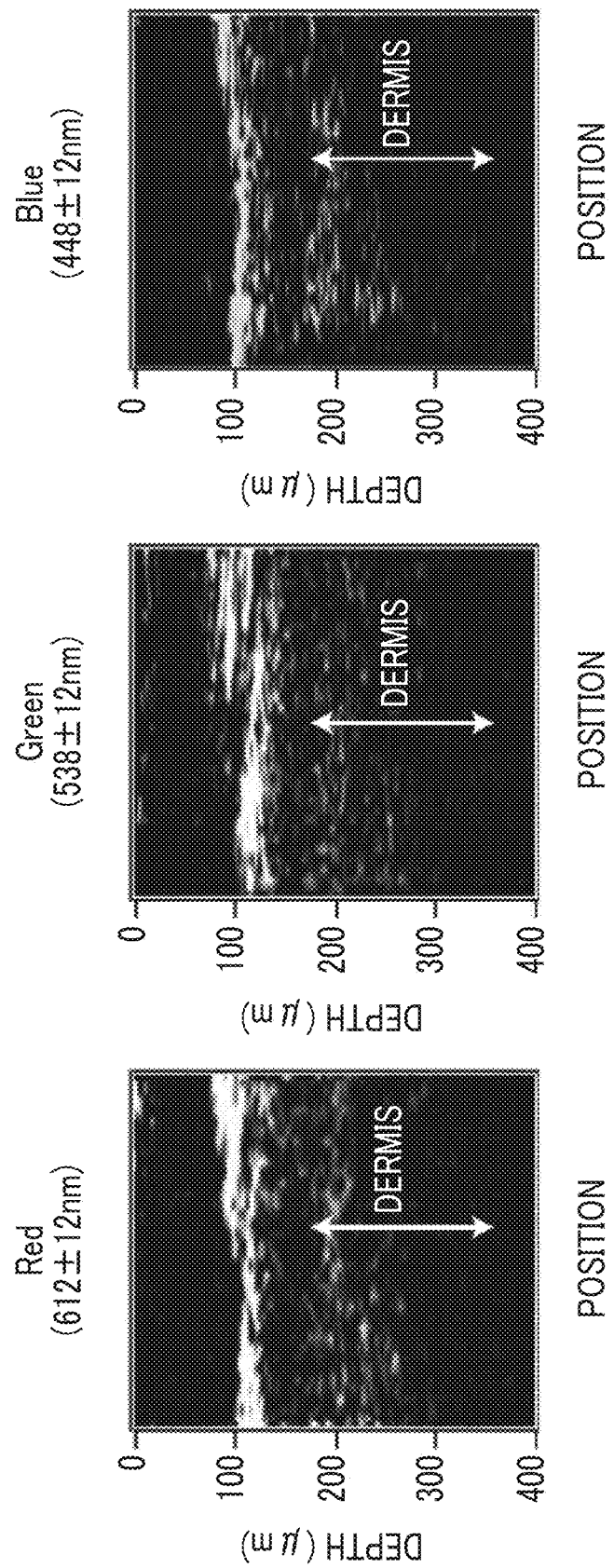
FIG. 12 illustrates OCT images acquired in red, green, and blue wavelength ranges acquired by human skin measurement in an optical coherence tomography apparatus according to this embodiment.

The inventors performed one-shot imaging for the human skin with the OCT apparatus 1 having the configuration illustrated in FIG. 1 to obtain R, G, and B OCT images. It was found that a red OCT image, a green OCT image, and a blue OCT image illustrated in FIG. 12 could be obtained by the frequency analysis of the original signal processing unit 51 of the image generation unit 50. In FIG. 12, a portion that is in the vicinity of 100 μm on the vertical axis is the surface of the human skin and a region deeper than the portion is the inside of the skin. A signal in the vicinity of a depth of 0 to 30 μm from the surface position indicates the keratin, a dark region at a depth of 30 to 100 μm is the epidermis, and a region at a depth of 100 μm or more is the dermis. The epidermis is relatively transparent and the amount of scattered light in the epidermis is small. Since collagen is included in the dermis, the intensity of scattered light in the dermis is higher than that in the epidermis. It is clear that a signal from the dermis can be observed in each of R, G, and B and measurement at the same place can be performed. In addition, observation up to a very deep range of 400 μm is possible.

The stimulus values X, Y, and Z in the CIE-XYZ color system can be calculated using the OCT image data (original data) of these three colors and can be converted into R, G, and B values to obtain a full-color image. However, as described above, the use of the original data including the influence of light attenuation caused by, for example, color makes it difficult to display a true color. For this reason, the image generation unit 50 performs a correction process for the OCT image data of each color to generate corrected data.

A detailed correction data calculation method in a case in which the correction processing unit 52 in the first configuration of the image generation unit 50 illustrated in FIG. 4 is provided will be described.

Figure 13A:
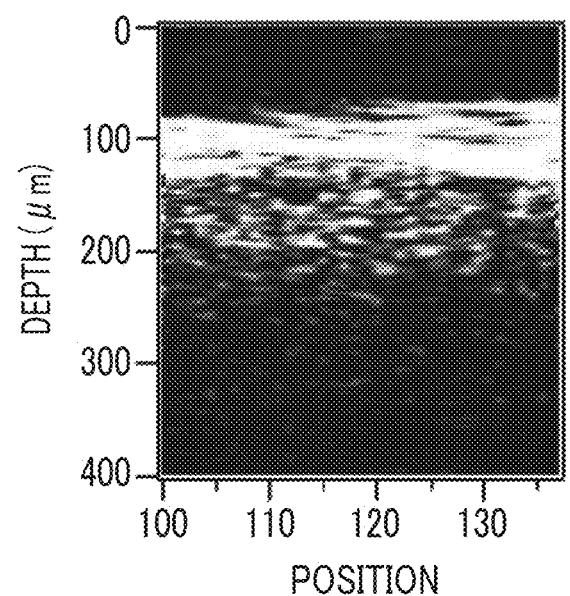
FIG. 13A is a diagram illustrating a first correction method and illustrates an OCT image acquired in the green wavelength range.
Figure 13B:
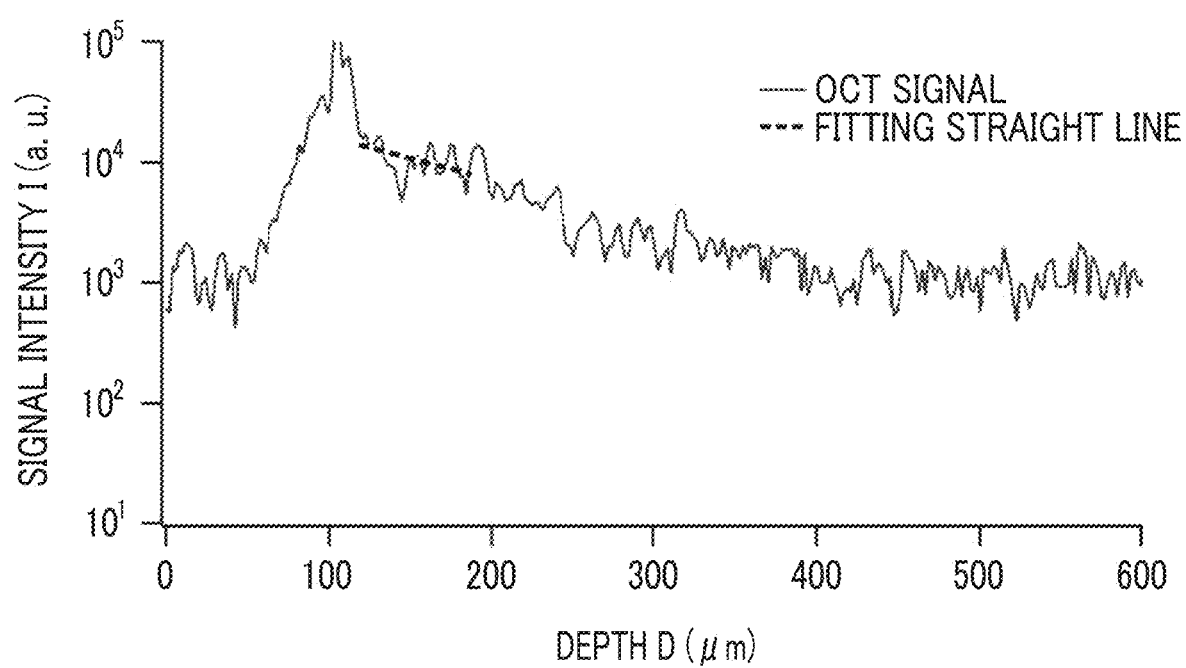
FIG. 13B is a diagram illustrating the first correction method and illustrates a one-dimensional profile of signal intensity acquired from image data illustrated in FIG. 13A in a depth direction.

FIG. 13A illustrates a green OCT image of the human skin and FIG. 13B illustrates the intensity of an OCT signal with respect to the depth extracted from the OCT image data illustrated in FIG. 13A. As illustrated in FIG. 13A, a region which is in the vicinity of 100 μm on the vertical axis and is displayed in white is the keratin and a region in the vicinity of 120 to 190 μm on the vertical axis is the epidermis. Fitting is performed for an epidermis region (first depth region) of the OCT signal profile of FIG. 13B corresponding to the image by a least square method with a line represented by $\exp(-\alpha D)+C$ (a dashed line in FIG. 13B) to calculate an attenuation constant $\alpha$ for the epidermis region. In the fitting straight line, D is the depth and C is an apparatus constant (a value determined depending on the apparatus). According to the Lambert-Beer law, light intensity I is attenuated by $I=I0\times\exp(-\alpha D)$ in a depth direction D with respect to intensity I0 in the surface that is not attenuated. Therefore, signal intensity in a region (second depth region) deeper than the epidermis is multiplied by $I0/I=\exp(\alpha D)$ to calculate true OCT signal intensity in a case in which there is no influence of the epidermis. In addition, the intensity of the OCT signal is strictly attenuated by a reciprocating optical path 2×D. In this correction calculation, there is no problem in a case in which the constant of 2 is handled as being included in a. Further, instead of the light intensity I, an electric field E may be used so as to be put on the straight line represented by $\sqrt{(\exp(-\alpha D))}+C$ and then the calculation may be performed. In this case, the same effect as described above is obtained.

The attenuation constant calculation unit 53 calculates an attenuation constant for the first depth region in the image data of each color, using the above-mentioned method. Then, the signal correction arithmetic unit 54 corrects the data of the second depth region with the calculated attenuation constant to calculate corrected data.

The color image generation unit 58 generates full-color image data on the basis of the corrected data.

Figure 14:
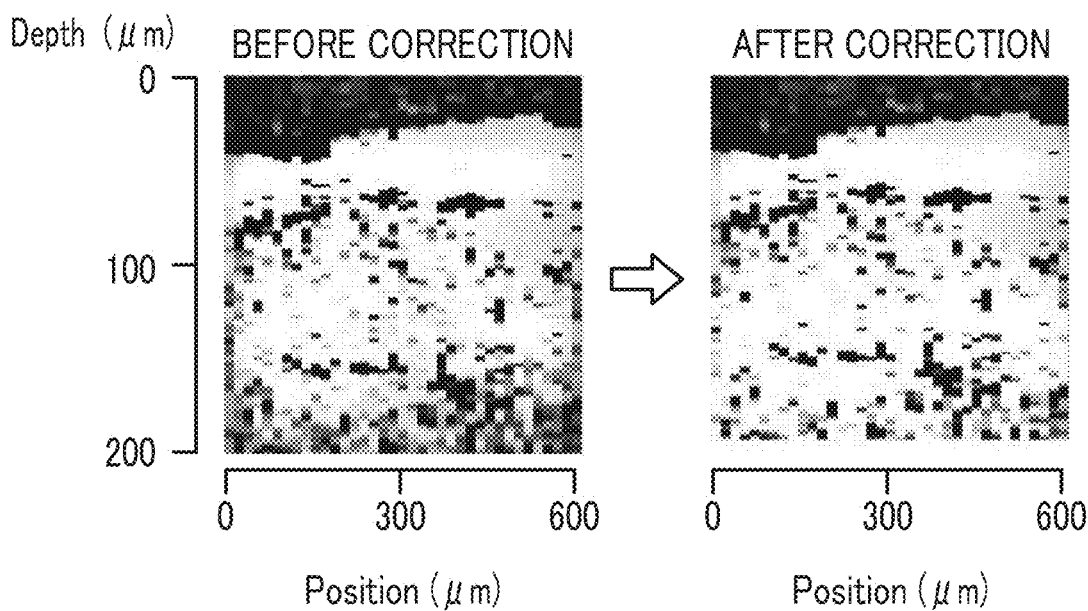
FIG. 14 is a diagram illustrating a full-color OCT image before and after correction by the first correction method.

FIG. 14 illustrates a full-color OCT image (before correction) generated from the original data of each of R, G, and B which has not been subjected to the correction process and a full-color OCT image (after correction) generated from the corrected data corrected by the above-mentioned process. As can be seen from the comparison between the OCT images before and after correction illustrated in FIG. 14, the attenuation of light intensity inside the measurement target is corrected and light intensity increases after correction. Therefore, the percentage of white scattered light in the dermis region increases. FIG. 13A illustrates an example for describing the correction method and FIG. 14 illustrates an example of the full-color OCT image corrected by the same correction method. The measurement targets in FIG. 13A and FIG. 14 are not the same.

A detailed correction data calculation method in a case in which the correction processing unit 52 in the second configuration of the image generation unit 50 illustrated in FIG. 5 is provided will be described.

First, the spectral reflectance measurement unit 59 measures the spectral reflectance of the same position as an OCT image measurement position of the measurement target in the surface. Then, the melanin concentration of the epidermis (first depth region) is estimated from the spectral reflectance. Specifically, it is assumed that the human skin has a three-layer structure including the epidermis (here, the keratin is included in the epidermis) and the dermis having a two-layer structure. Monte Carlo calculation is performed for the three-layer structure and melanin and hemoglobin concentrations are calculated on the basis of a scattering coefficient of the skin described in the known literature and melanin and hemoglobin absorption spectra. In addition, it is assumed that melanin is contained in the epidermis, no pigments are contained in an upper layer in the dermis having the two-layer structure, and hemoglobin is contained in a lower layer which is a deeper region in the dermis. Here, it is assumed that, of two layers forming the dermis, the upper layer is the second depth region. The lower layer of the dermis is a deep region that is not capable of being acquired by the OCT image. This calculation was performed assuming that the thickness of the epidermis was 100 μm, a region with a thickness of 200 μm corresponding to the upper layer of the dermis, particularly, the vicinity of the papillary layer was a region without a pigment, and the thickness of the lower layer of the dermis was 2.8 mm. In addition, the scattering coefficients of the epidermis and the dermis were equal to each other. Further, it was assumed that, for hemoglobin in the blood, the concentration ratio of oxidized hemoglobin to reduced hemoglobin was 1:1. Under the above-mentioned conditions, the melanin concentration and hemoglobin concentration were changed and the spectral reflectance of a visible region was calculated by the Monte Carlo method to calculate melanin concentration and hemoglobin concentration in a case in which the spectral reflectance was closest to the measured value.

Figure 15:
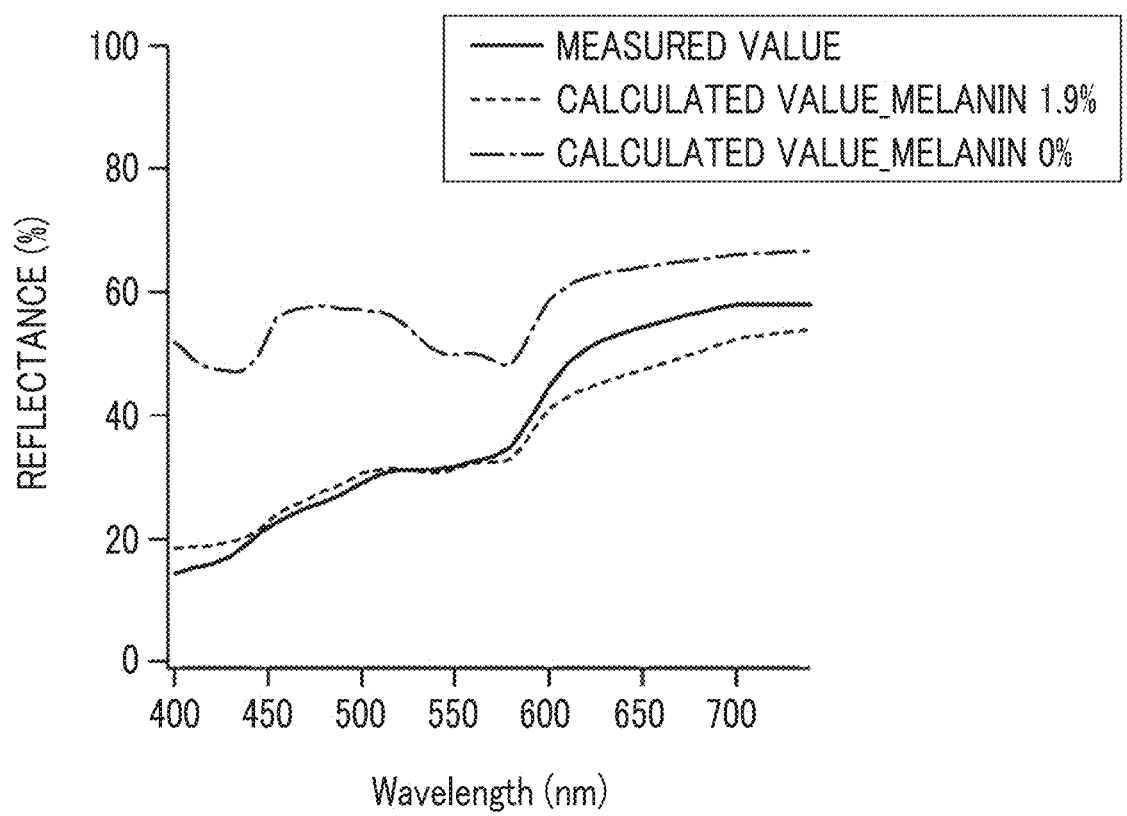
FIG. 15 is a diagram illustrating a second correction method and illustrates spectral reflectance for a measurement target.

FIG. 15 illustrates the spectral reflectance of the human skin measured by a reflectance measurement device V-7200 manufactured by JASCO Corporation, spectral reflectance (melanin concentration: 1.9%) which is closest to the measured value of the spectral reflectance and is calculated by the above-mentioned method, and spectral reflectance in a case in which factors are the same as described above except the melanin concentration in the epidermis (first depth region) and the melanin concentration is 0%.

As illustrated in FIG. 15, the spectral reflectance obtained by the simulation in which the melanin concentration is 1.9% is matched with the measured spectral reflectance with high accuracy and the calculated melanin concentration in the epidermis is 1.9%. As such, the attenuation of light by melanin in the epidermis which can be calculated from the melanin concentration in the epidermis is corrected with respect to signal intensity from the dermis (second depth region). In this way, the color tomographic image of the dermis which is not affected by the color of the epidermis is obtained.

The pigment concentration calculation unit 55 performs Monte Carlo calculation on the basis of, for example, the spectral reflectance obtained from the surface of the measurement target as described above, the known structure of the measurement target, and the pigment contained in the measurement target to calculate the pigment concentration of the first depth region. Then, the signal correction arithmetic unit 56 corrects the data of the second depth region with the amount of attenuation obtained from the pigment concentration to calculate corrected data.

The color image generation unit 58 generates full-color image data on the basis of the corrected data.

Figure 16:
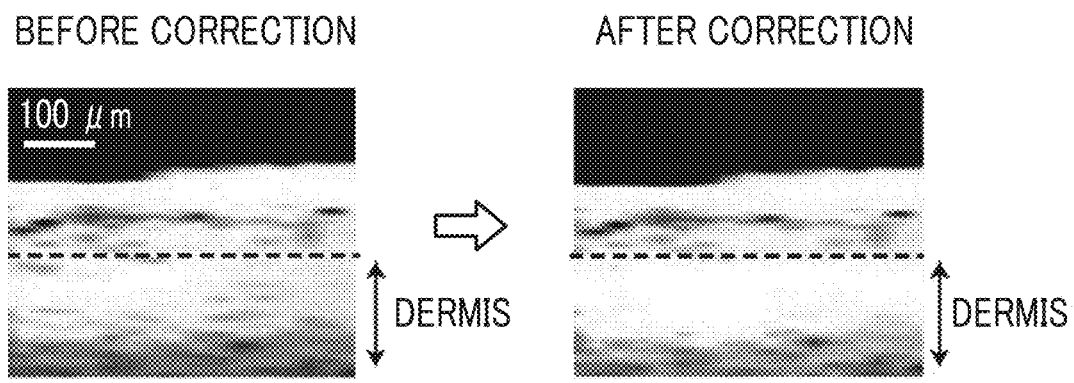
FIG. 16 is a diagram illustrating a full-color OCT image before and after correction by the second correction method.

FIG. 16 illustrates a full-color OCT image (before correction) generated from the original data of each of R, G, and B which has not been subjected to the correction process and a full-color OCT image (after correction) generated from the corrected data corrected by the above-mentioned process. As can be seen from the comparison between the OCT images before and after correction illustrated in FIG. 16, the attenuation of light intensity inside the measurement target is corrected and light intensity increases after correction. Therefore, the percentage of white scattered light in the dermis region increases and the dermis is brightened by the correction.

As described above, the process of correcting the data of the lower layer (second depth region) with the attenuation constant for the region in the upper layer (first depth region) is performed to reproduce the true color of the measurement target and an OCT image of a color closer to the true color than that at least in a state in which the correction process is not performed.

The case in which the measurement target is the human skin has been described above. Even in a case in which the measurement target is a coating film (a coating film formed on the base), it is obvious that this configuration can be used as means for non-invasively measuring the true color in the depth direction.

The spectral-domain (SD) OCT apparatus that uses a broadband white light source and acquires a depth distribution from the spectrum of interference light has been described above. However, the invention may be applied to a time-domain (TD) OCT apparatus provided with a mechanism for mechanically changing an optical path length. In a case in which the measurement target is a stationary object, there is no particular problem regardless of whether the OCT apparatus is the TD type or the SD type. In a case in which the measurement target is an object such as, the human skin or an animal skin, which is likely to cause blurring, it is preferable to use the SD type having the above-mentioned configuration that can capture images with one shot.

An embodiment of a measurement method according to the invention using the optical coherence tomography apparatus according to this embodiment will be described.

Here, a case in which the measurement target is the human skin will be described. However, the measurement method is the same as that in a case in which the measurement target is, for example, a coating film. The skin (human skin) of a subject is irradiated with the measurement light and interference light of the measurement light and the reference light is spectroscopically detected. Frequency analysis is performed for the interference light to generate two-dimensional image data. In addition, a correction process for correcting light attenuation in the depth direction is performed to generate a full-color OCT image from the correction image data of three colors of R, G, and B. Further, optical features in the surface of the human skin or inside the human skin are calculated from the spectroscopically detected interference light. Then, the full-color OCT image and the optical features are displayed on the image display device. The image and the optical features may be displayed on the image display device at the same time or may be sequentially displayed on the image display device.

The optical features include the intensity of reflected light at any position on the surface of the human skin or inside the human skin acquired from the image data of a specific color (for example, red), the one-dimensional profile of the intensity of the reflected light in the depth direction, and an attenuation constant. For example, the numerical value or graph of each of the optical features is displayed.

As described above, in a case in which the full-color OCT image and the optical feature are displayed by the measurement method according to the invention, a measurer or a diagnostician can easily evaluate the state of the skin from the displayed content. For example, samples for brightness and a profile in the depth direction and in the OCT image may be acquired from a large number of subjects, numerical ranges that can be regarded as normality and abnormality may be prepared as data in an analysis unit in advance. Then, the numerical values and the measured values may be compared and the evaluation results, such as normality and abnormality, may be displayed.

In addition, for cosmetics or medicines to be evaluated, OCT images are acquired before and after the cosmetics or the medicines are applied onto the human skin, optical features are calculated, and the OCT images before and after the application and the optical features are simultaneously or sequentially displayed on the image display device. This configuration makes it possible to visually check a change in the surface of the skin and the inside of the skin before and after the cosmetic or the medicines are applied and to evaluate, for example, the effect of the applied products. In addition, it is preferable to simultaneously display, for example, the images or numerical values to be compared with each other on the image display device in order to facilitate the comparison. A difference between the OCT images before and after the application or a difference between the optical features may be calculated and these differences may be displayed as changes before and after the application on the image display device.

in a case in which the optical coherence tomography apparatus according to the invention is used, it is possible to show a true color inside each skin, such as a white skin or a black skin (here, the light or dark skin of the yellow race is assumed), a transparent skin, or a dull and it can be expected to present new values on the distribution of pigments inside the skin or a color expression mechanism.

Further, in a case in which the measurement method using the optical coherence tomography apparatus according to the invention is used, it is possible to easily evaluate the influence of active ingredients of, for example, cosmetics, quasi-drugs, or medicines on the skin. Specifically, the measurement method is also useful to evaluate the effects of, for example, skin roughness improving agents, moisturizing agents, whitening agents, anti-wrinkle agents, acne improving agents, thickened keratin improving agents, turnover improving agents, pore astringents, hair growing agents, antioxidants. However, the application of the measurement method is not particularly limited.

The optical coherence tomography apparatus according to the invention is an apparatus that can obtain a full-color OCT image in real time with a high temporal resolution and can be used for skin diagnosis and analysis including injuries and diseases, the monitoring of the production of films, or the analysis of the color images of, for example, coating films provided on the surfaces of various bases in the tomographic direction, regardless of the cosmetics. However, the measurement target is not limited. The two-dimensional OCT image has been described above. However, the OCT apparatus may be provided with a scanning unit that performs scanning in a direction perpendicular to the emission line of the linear measurement light and form a three-dimensional OCT image.

EXPLANATION OF REFERENCES

1: optical coherence tomography apparatus (OCT apparatus)
3: light splitting unit (quartz plate)
4: multiplexing unit
5: quartz plate
6: reflecting member (mirror)
10: light source unit
11: light source
12: spectral shaping unit
20: measurement light emission optical system
21, 25, 26: cylindrical lens
27: dimming filter
28: optical path adjustment mechanism
30B, 30G, 30R: interference light detection unit
31: spectroscope
32: two-dimensional optical detector
35, 36, 37: imaging lens
50: image generation unit
51: original signal processing unit
52: correction processing unit
53: attenuation constant calculation unit
54, 56: signal correction arithmetic unit
55: pigment concentration calculation unit
58: color image generation unit
59: spectral reflectance measurement unit
60: image display device
80: skin surface
82: keratin
84: epidermis
86: dermis
90: base
92: underlying layer
94: coloring layer
96: clear coating layer
98: coating film
101: glass container
102: gelatin

What is claimed is:

1. A measurement method using an optical coherence tomography apparatus comprising:
a light source unit that emits low-coherent light with a red wavelength, low-coherent light with a green wavelength, and low-coherent light with a blue wavelength at the same time;
a light splitting unit that splits the low-coherent light emitted from the light source unit into measurement light and reference light;
a measurement light emission optical system that irradiates a measurement target with the measurement light;
a multiplexing unit that multiplexes the reference light and light reflected from the measurement target in a case in which the measurement target is irradiated with the measurement light;
an interference light detection unit that detects interference light of the reflected light and the reference light multiplexed by the multiplexing unit; and
an image generation unit that generates an optical coherence tomographic image of the measurement target from the interference light detected by the interference light detection unit,
wherein the image generation unit calculates an attenuation related value related to attenuation of signal intensity of the interference light of the red wavelength, the green wavelength, and the blue wavelength in a first depth region, corrects the signal intensity in a second depth region deeper than the first depth region according to the attenuation related value to calculate a correction signal for the interference light, and generates a full-color optical coherence tomographic image using the correction signals calculated for each of the red wavelength, the green wavelength, and the blue wavelength;
the method comprising:
irradiating a measurement target with the measurement light;
detecting the interference light;
generating an optical coherence tomographic image of the measurement target;
displaying the optical coherence tomographic image on an image display device;
calculating optical features on a surface of the measurement target or inside the measurement target from the interference light; and
displaying the optical features on the image display device.

2. The measurement method according to claim 1, wherein intensity of reflected light at any position on the surface of the measurement target or inside the measurement target, a profile of the intensity of the reflected light in a depth direction, or an attenuation constant is calculated as the optical features.

3. The measurement method according to claim 2, wherein the measurement target is a coating film.

4. The measurement method according to claim 3, wherein the measurement target is a human skin.

5. The measurement method according to claim 4, wherein the optical coherence tomographic images of the human skin are generated before and after any cosmetic or medicine is applied to the human skin,
the optical features are calculated, and
the optical features and the optical coherence tomographic images before and after the application are displayed on the image display device.

* * * * *